United States Patent
Brackett

(10) Patent No.: US 6,525,334 B1
(45) Date of Patent: Feb. 25, 2003

(54) SYSTEM AND METHOD FOR DETECTING EROSION CAUSED BY PARTICLES IN A FLUID

(75) Inventor: Robert R. Brackett, Cookeville, TN (US)

(73) Assignee: Fleetguard, Inc., Nashville, TN (US)

( * ) Notice: Subject to any disclaimer, the term of this patent is extended or adjusted under 35 U.S.C. 154(b) by 0 days.

(21) Appl. No.: 09/444,428

(22) Filed: Nov. 19, 1999

(51) Int. Cl.[7] .............................................. G01N 15/06
(52) U.S. Cl. .................... 250/573; 250/222.2; 73/53.07
(58) Field of Search ................................. 250/573, 574, 250/222.2, 221; 180/335, 336, 415, 422; 73/53.07, 53.04, 53.05, 53.06; 356/70, 436–438, 441; 340/618–620

(56) References Cited

U.S. PATENT DOCUMENTS

| | | | |
|---|---|---|---|
| 2,440,691 A | 5/1948 | Jira .............................. 201/76 |
| 2,529,436 A | 11/1950 | Weber et al. .................. 178/44 |
| 3,678,273 A | 7/1972 | Lewis .......................... 250/83 |
| 3,753,257 A | 8/1973 | Arnold ........................ 340/236 |
| 3,818,470 A | * 6/1974 | Hirsbrunner et al. ........ 250/577 |
| 3,876,935 A | 4/1975 | Guillermie et al. ........... 324/65 |
| 4,305,278 A | 12/1981 | Stewart et al. ................. 73/61 |
| 4,338,563 A | 7/1982 | Rhoades et al. .............. 324/65 |
| 4,646,070 A | 2/1987 | Yasuhara et al. ........... 340/603 |
| 4,675,662 A | 6/1987 | Kondo et al. ................ 340/631 |
| 4,733,556 A | 3/1988 | Meitzler et al. ................ 73/64 |
| 4,741,200 A | 5/1988 | Hammerle ...................... 73/54 |
| 4,741,204 A | 5/1988 | Luck et al. .................... 73/116 |
| 5,049,742 A | 9/1991 | Hosonuma et al. ......... 250/301 |
| 5,211,677 A | 5/1993 | Sargeant et al. ........... 83/61.71 |
| 5,332,961 A | 7/1994 | Hammerle .................. 324/700 |
| 5,377,531 A | 1/1995 | Gomm ....................... 73/53.05 |

* cited by examiner

*Primary Examiner*—Que T. Le
(74) *Attorney, Agent, or Firm*—Woodard, Emhardt, Naughton Moriarty & McNett LLP

(57) ABSTRACT

An abrasive particle detention system includes a fluid circulation system, a probe assembly, a monitoring circuit, and an operator indicator. The probe assembly includes an orifice from which a stream of fluid emerges, and a probe having a face upon which the stream at least partially impinges. The probe face includes an insulative substrate and a conductive film formed on the substrate. Abrasive particles in the fluid stream abrade the conductive film, changing its electrical resistance. A monitoring circuit is utilized to observe these changes, and when they correspondence to a concentration above a pre-selected level, an operation indicator is triggered. The system may include an electronic controller coupled to the monitoring circuit, which can account for variables such as temperature, viscosity, and/or pressure in the fluid circulation system.

18 Claims, 8 Drawing Sheets

SYSTEM AND METHOD FOR DETECTING EROSION CAUSED BY PARTICLES IN A FLUID

BACKGROUND OF THE INVENTION

The present invention relates to detecting abrasive particles in a fluid. More particularly, but not exclusively, the present invention relates to an abrasive particle sensor that includes an electrically conductive film on an insulating substrate. Many machines employ fluid systems, to reduce wear, for heat transfer, to transfer power, etc. Common examples include hydraulic systems, pneumatic systems, pumping systems, air induction systems, oil lubrication systems, and water cooling systems. When abrasive particles accumulate in such systems they can cause equipment wear. In order to reduce parts wear, in many cases, the fluid is simply changed on a periodic basis. However, if abrasive particles accumulate at an unexpected rate, this practice results in either excessive wear, or unnecessary fluid changes. It is therefore useful to ascertain abrasive particle accumulation in situ. In many situations, previous attempts to monitor particle content of a fluid have been found to lack desired sensitivity, robustness, and/or cost effectiveness. Thus, there is a demand for further contributions in the area of abrasive particle monitoring technology.

SUMMARY OF THE INVENTION

One form of the present invention is a unique technique for monitoring particle content of a fluid. Other forms include unique systems and methods for monitoring particles with an electrically conductive member sensitive to particle erosion.

Another form of the present invention includes a method of observing erosion caused by particles in a fluid. Erosion is evaluated in accordance with one or more characteristics of an electrically conductive member that is exposed to the particles. For one variety of this form, the conductive member is at least partially composed of a metal, such as aluminum (Al), gold (Au), palladium (Pd), platinum (Pt), titanium (Ti), or alloys thereof. In another variety of this form, the conductive member is at least partially composed of a nitride, oxide, or silicide containing metal, such as tantalum nitride (TaN).

In still another form, an electrically conductive pathway senses erosion caused by particles in a fluid stream delivered from an orifice. The ratio of the cross-conductive width of the pathway to the diameter of the orifice is preferably between about 0.5 and about 1.5, and more preferably between about 0.75 and about 1.25.

A further form of the present invention includes a system for observing erosion caused by particles in a fluid by monitoring their effect on an electrically conductive film comprising aluminum (Al), gold (Au), palladium (Pd), platinum (Pt), titanium (Ti), tungsten (W), tantalum (Ta), rhodium (Rh), or alloys thereof; and/or a silicide, oxide, or nitride containing at least one metal element such as tantalum nitride (TaN). This system includes a fluid subsystem, a probe carrying the conductive film, and an electrical monitoring circuit for measuring changes in one or more electrical properties of the film.

Yet another form of the present invention includes a system for detecting particles in a fluid. The system includes an electrically conductive member in contact with the fluid and an electronic controller. The electronic controller receives one or more signals corresponding to one or more characteristics of the conductive member from which the presence of particles in the fluid may be determined. The electronic controller can adjust signals from the conductive member to account for variations due to factors such as temperature, viscosity, and pressure.

In another form, an engine with an air induction system and a particle sensor is provided that includes an electrically conductive particle sensing member in fluid communication with air from the induction system. An electrical monitoring circuit includes an electrical pathway that is at least partially provided by the particle sensing member. This circuit monitors variation of a property of the member corresponding to electrical resistance. This resistance changes in accordance with erosion of the member by particles from the air induction system.

Further objects, forms, embodiments, features, advantages, aspects, and benefits of the present invention will become apparent from the description and drawings contained herein.

BRIEF DESCRIPTION OF THE DRAWINGS

FIG. 6 is presented in section along section lines 6—6 shown in FIG. 5.

DESCRIPTION OF THE PREFERRED EMBODIMENTS

Figure 1:
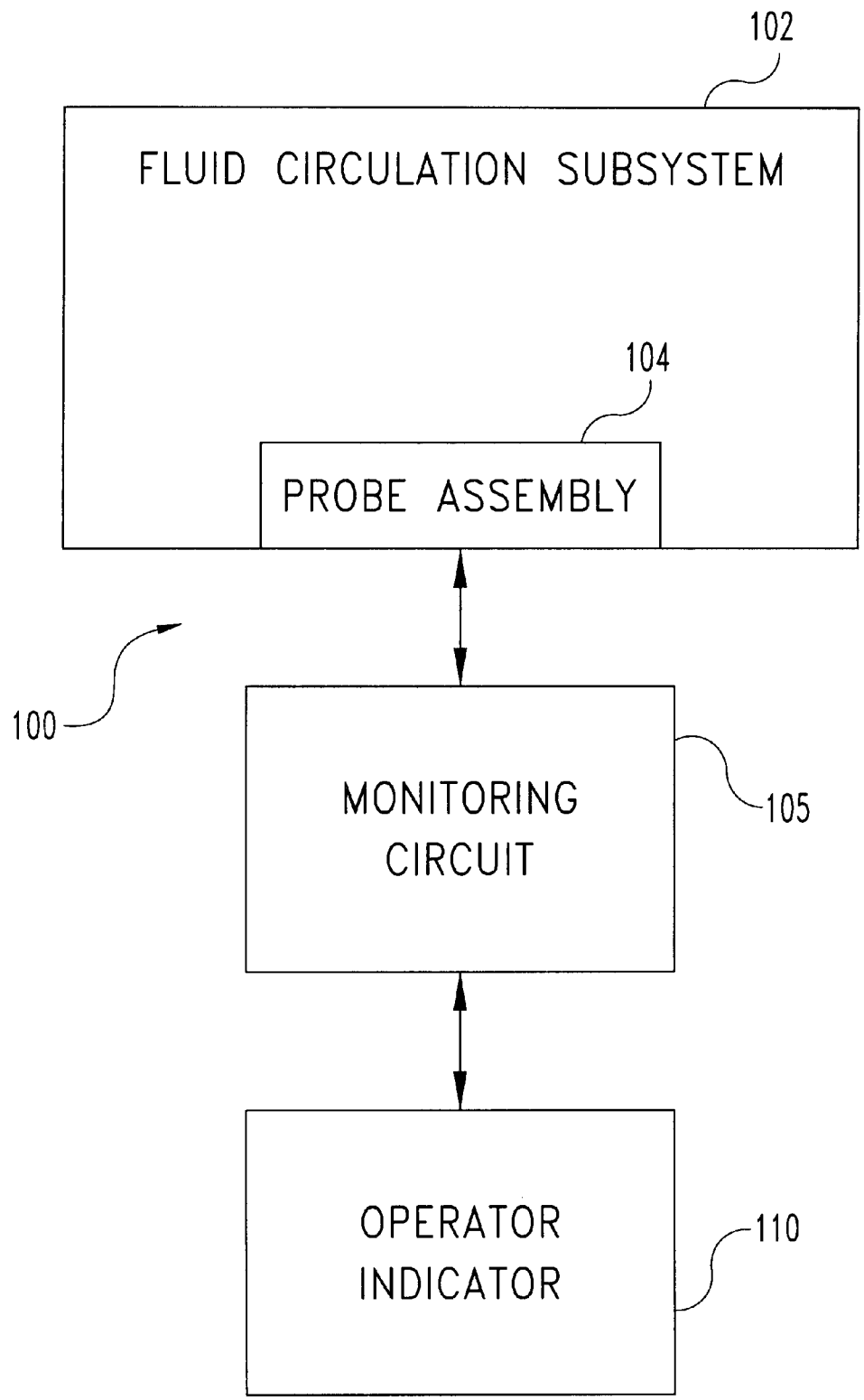
FIG. 1 is a block diagram of one embodiment of an erosion detection system according to the present invention.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

FIG. 1 schematically depicts erosion detection system 100 of one embodiment of the present invention. System 100 includes fluid circulation system 102. System 102 can be arranged to circulate a fluid for one or more purposes such as lubrication, heat transfer, power transfer; fluid quality testing, or can be otherwise applied as would occur to those skilled in the art. Typically, undesirable particles tend to accumulate in the fluid of system 102 from various sources during operation. Over time, these particles can potentially damage components that come in contact with the fluid.

To detect and report the presence of such particles, system 100 also includes probe assembly 104, monitoring circuit 105, and indicator 110. Probe assembly 104 is electrically coupled to monitoring circuit 105, and monitoring circuit 105 is operably coupled to operator indicator 110. At least a portion of probe assembly 104 is altered by contact with particles carried in the fluid. Monitoring circuit 105 detects this alteration to provide one or more signals indicative of particle content. Operator indicator 110 is responsive to monitoring circuit 105 to provide a corresponding output to an operator.

Figure 2:
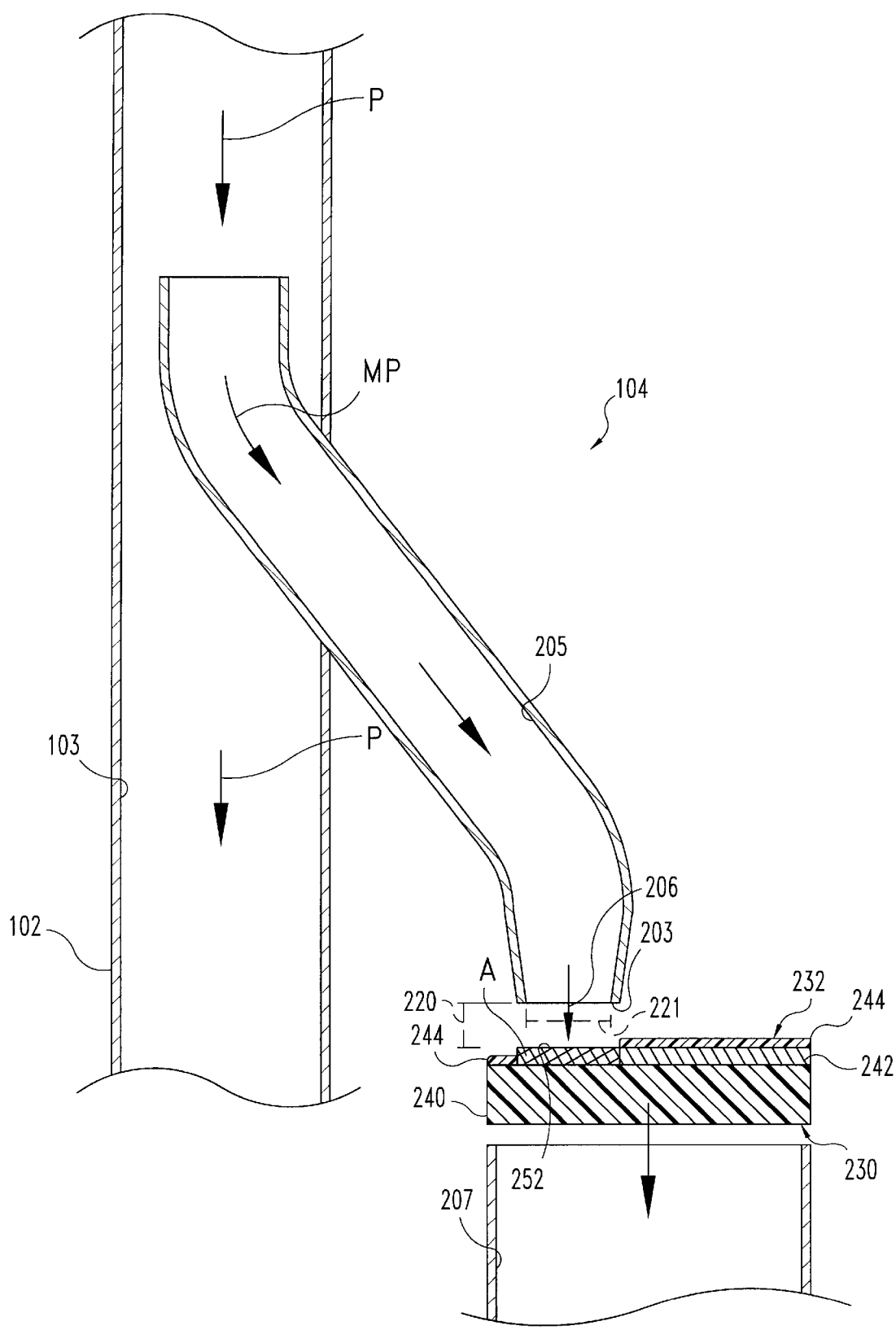
FIG. 2 is a partially diagrammatic, sectional view of the probe assembly shown in FIG. 1.

Referring now to FIG. 2, details of probe assembly 104 are further illustrated. Probe assembly 104 includes fluid monitoring conduit 205 in fluid communication with conduit 103 of system 102. Conduit 103 defines circulation fluid path P and conduit 205 defines monitoring path MP as represented by like labeled arrows. Conduit 205 diverts some or all of the fluid circulating along path P to path MP. Conduit 205 terminates in orifice 203. Orifice 203 has minimum diameter 221. Pressure in system 100 causes a stream of fluid 206 to discharge through orifice 203 in the form of a jet. To provide this jet, probe assembly 104 is arranged to provide a differential pressure (dP) across orifice 203. In one embodiment, orifice 203 and conduit 205 are sized and arranged relative to conduit 103 to sample fluid with a flow velocity through conduit 205 that is about the same as the flow velocity in conduit 103. Probe assembly may include one or more flow regulators, flow limiters, and/or other devices directed to fluid flow control. Alternatively or additionally, probe assembly 104 may be arranged to deliver particles through stream 206 at about the same density per unit volume of the fluid and with about the same size particle distribution as realized in system 102.

Probe assembly 104 also includes probe 230 spaced apart from orifice 203 by gap distance 220. Fluid exiting orifice 203 travels minimum gap distance 220, contacting probe 230. The jet of fluid stream 206 initially impinges on face 232 of probe 230. In one embodiment, the ratio of the minimum gap distance 220 to the minimum orifice diameter 221 is between 1 and 3. In other embodiments, a gap ratio outside this range may be utilized. For example, a larger gap ratio (>3) may be used to reduce premature wear where the fluid viscosity is very low. After contacting probe 230, fluid exiting orifice 203 flows into collection conduit 207 of probe assembly 104 to be returned to conduit 103 of subsystem 102. The returning fluid is at a lower pressure than in conduit 205 to provide the differential pressure necessary to create a fluid jet of sufficient velocity to elicit a response from the sensor. In one embodiment, fluid from conduit 207 rejoins fluid from conduit 103 in a sump area of fluid circulation system 102, although other arrangements may be utilized as would occur to those skilled in the art.

Figure 3:
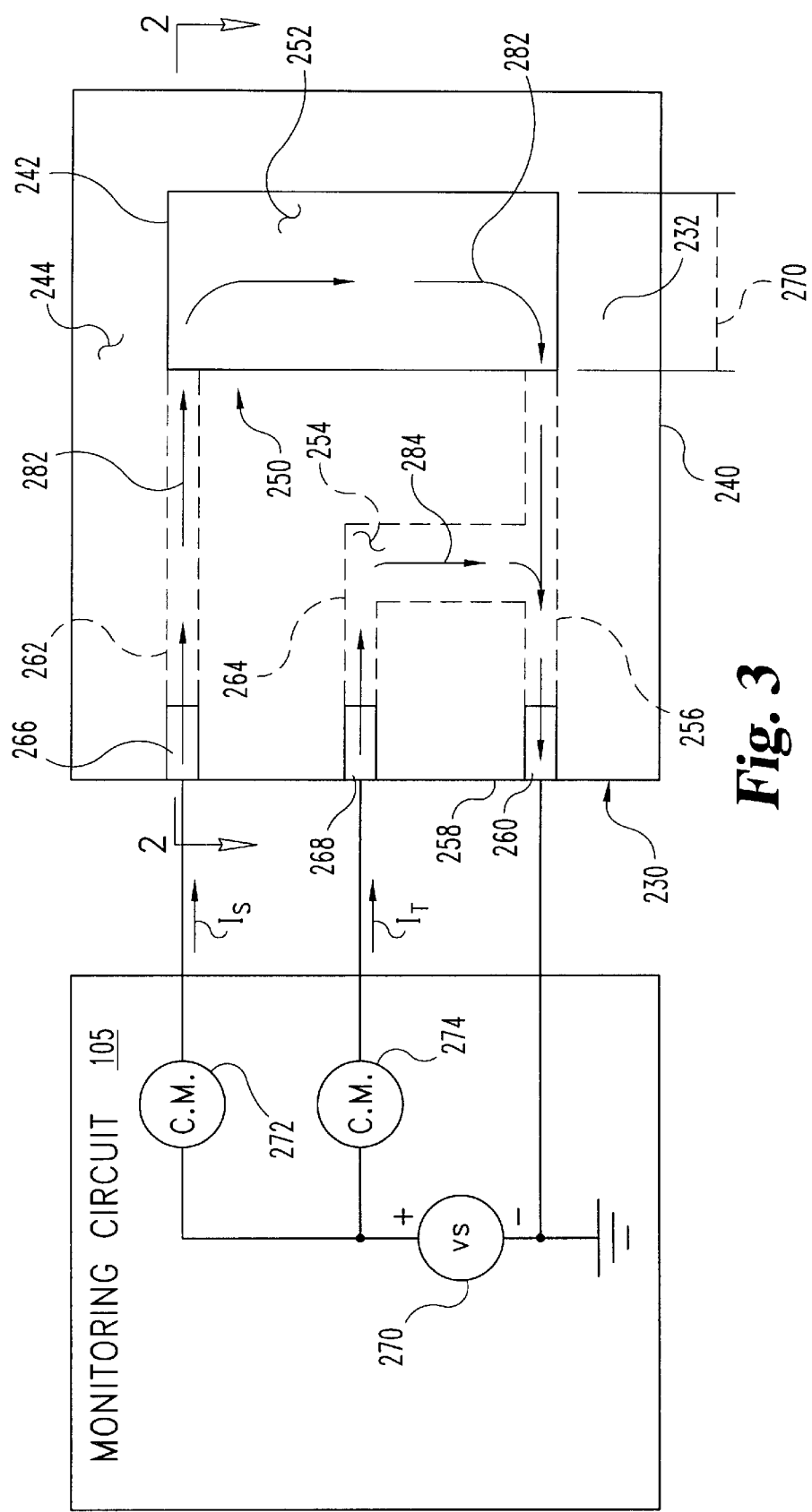
FIG. 3 is a partial diagrammatic view of the probe shown in FIG. 2.

Referring additionally to FIG. 3, further details of probe 230 are illustrated. Probe 230 has an electrically insulative substrate 240 carrying an electrically conductive film 242. Conductive film 242 is arranged in pattern 250. Dielectric coating 244 partially covers pattern 250. Portions of pattern 250 covered by coating 244 are schematically shown in broken line form. Typically, coating 244 is an electrically insulative composition selected to be resistant to wear by particles carried in the fluid so that portions of pattern 250 covered by coating 244 are not exposed to particles during normal use of probe 230. Pattern 250 defines detection region 252 and compensation region 254. One area of pattern 250 not covered by coating 244 is detection region 252. Regions 252, 254 are electrically coupled by trace 256 of pattern 250. Trace 256 terminates at edge 258 of probe 230 in contact area 260. Pattern 250 further defines trace 262 electrically coupled to detection region 252 and trace 264 electrically coupled to compensation region 254. Traces 262, 264 terminate at edge 258 in contact areas 266, 268, respectively. Contact areas 260, 266, 268 are arranged for electrical interconnection to monitoring circuit 105. Also, at least a portion of contact areas 260, 266, 268 can be left uncovered by coating 244 (as shown) to facilitate electrical interconnection.

FIG. 3 also illustrates further details concerning monitoring circuit 105. Monitoring circuit 105 is schematically illustrated with independent voltage source 270 having a common ground connection to trace 256. Also represented are two current monitors (C.M.s) 272, 274 electrically coupled in series with traces 262, 264, respectively. Current monitors 272, 274 are also each coupled at a common node to voltage source 270. When a suitable electric potential is supplied by voltage source 270, two conductive branches or pathways 282, 284 are defined through conductive film 242. Electrical currents along pathways 282, 284 are detected with monitors 272, 274, and are labeled $I_S$, $I_T$, respectively. Preferably, detection region 252 has a minimum cross-conductive width 270 relative to current $I_S$ between about 0.5 and about 1.5 times the minimum diameter 221 of orifice 203. More preferably, the minimum cross-conductive width 270 is between about 0.75 and about 1.25 times the minimum diameter 221 of orifice 203. One example of the minimum conductive cross-sectional area corresponding to width 270 is area A symbolically illustrated by a cross-hatch pattern in FIG. 2. Area A and width 270 are each normal to the current density vector corresponding to current $I_S$ that passes through area A and crosses width 270.

It should be understood that conductive film 242 defines an amount of electrical resistance for each pathway 282, 284. For a generally constant D.C. voltage output $V_{DC}$ from source 270, and a negligible resistance contributed by current monitors 272, 274; resistance $R_S$, $R_T$ of conductive film 242 comprising pathways 282, 284; respectively is determined in accordance with Ohm's law as follows;

$R_S = V_{DC}/I_S$; and $R_T = V_{DC}/I_T$.

Referring generally to FIGS. 1–3, certain aspects of the operation of system 100 are next described. During operation, fluid stream 206 contacts probe face 232 of probe assembly 104 as illustrated in FIG. 2. Fluid stream 206 directly contacts the exposed detection region 252. When fluid stream 206 carries particles with sufficient momentum and of sufficient hardness relative to region 252, then these particles gradually erode region 252, changing the minimum cross-section of film 242 through which current $I_S$ flows. Accordingly, electrical resistance $R_S$ changes with the mechanical alteration of detection region 252 by particles carried in fluid stream 206. This change in $R_S$ can be used to gauge particle content and predict fluid quality in terms of particle content.

For some applications, it may be desirable to compensate for changes in $R_S$ due to temperature. In contrast to detection region 252, compensation region 254 of electrically conductive film 242 is protected from particle erosion by coating 244. Consequently, electrical resistance $R_T$ does not appreciably change in response to particles in the fluid. However, compensation region 254 is in such an arrangement relative to detection region 252 that compensation region 254 is generally at about the same temperature as detection region 252 during steady state operation of subsystem 102. For this arrangement, temperature-induced change occurs in substantially the same amount for both $R_S$ and $R_T$. Accordingly, for this embodiment a change in the ratio $P_R$ of the resistance offered by regions 252, 254, ($PR=R_S/R_T$), may be utilized as an indication of abrading particle content in the fluid of subsystem 102. In a further example, the rate of change of $P_R$ can be monitored. Furthermore, for such embodiments, ratio $P_R$ is indicative of change in the resistance of detection region 252 relative to compensation region 254 even when resistance or impedance of monitors 272, 274 is not insubstantial.

Monitoring circuit 105 includes conventional circuitry to monitor a property corresponding to $R_S$ or $P_R$. Monitoring circuit 105 is arranged using standard techniques to determine if the monitored property indicates an unacceptable particle level in the fluid to provide one or more corresponding signals to indicator 110. While monitoring circuit 105 includes voltage source 270 and current monitors 272, 274 to determine $R_S$ relative to $R_T$, it should be understood that other circuit arrangements may be utilized. For example, pathways 282, 284 may be utilized as two branches of a Wheatstone bridge arrangement. Indeed, there are numerous known circuit arrangements to determine resistance or a corresponding property. For example, according to Ohm's Law, where an applied voltage or current is known, an observed current or voltage, respectively, provides such a corresponding property. In another example, both current and voltage can be varied in a known relationship to provide a property corresponding to an unknown resistance. In still another example, a corresponding property can be an impedance or conductance. Moreover, the determination of whether the property corresponds to an unacceptable particle level can be performed in a number of ways. For example, one or more analog comparators may be used to compare a voltage or current corresponding to $R_S$ to a threshold level. In another example, a voltage or current corresponding to $R_S$ may be converted to a discrete form with a suitable Analog-to-Digital converter (A/D) to perform a digital comparison. It should be understood that $R_S$, $P_R$, or both may be nonlinear as erosion progresses. Monitoring circuit 105 may be arranged to adjust for expected nonlinearity to the extent desired.

Many embodiments of indicator 110 and its interface to monitoring circuit 105 are also envisioned. Operator indicator 110 can be of a visual type, such as a light; an audible type, such as a buzzer; or such other variety as would occur to the those skilled in the art. In one embodiment, indicator 110 is a buzzer, light, or both that provides a warning to an operator when the ratio $P_R$ exceeds a predetermined threshold corresponding to an unacceptable particle content in the fluid of subsystem 102, and is otherwise inactive. In another embodiment, a warning is triggered based on the rate of change of $P_R$.

In still another embodiment, indicator 110 provides a particle content indication relative to a range. In one example, a series of Light Emitting Diodes (LEDs) are utilized to provide a range of discrete levels corresponding to particle content, with one of the LEDs being lit to indicate the current level. In another example, an analog type of gauge is used with a pivoting needle to indicate the current value. In still another embodiment, a graphic display form of indicator 110 provides the operator output.

For a given application, the ease with which undesirable particles in the fluid can remove material comprising region 252, the resistivity of this material, and the minimum cross-sectional dimension of this material through which current flows are a few of the parameters that can have a bearing on probe performance. In certain preferred liquid fluid embodiments, a composition of region 252 includes aluminum (Al), gold (Au), palladium (pd), titanium (Ti), platinum (Pt), tungsten (W), tantalum (Ta), rhodium (Rh), or alloys thereof. For a preferred embodiment to detect particles entrained in a gaseous fluid such as air, a composition of region 252 includes tantalum nitride (TaN). For a further preferred gaseous fluid embodiments, a composition of region 252 includes a metal containing silicide, oxide, nitride, or any combination thereof.

In a more preferred embodiment, a composition comprised of at least 40% Au by weight is applied as a thin film to provide region 252. In a still more preferred embodiment, region 252 and optionally some or all of the remainder of conductive film 242 are composed of an alloy of gold (Au) and Palladium (Pd). In a most preferred embodiment, at least region 252 of conductive film 242 includes an Au/Pd alloy where the ratio of Au to Pd is in a range of about 2:3 to about 3:2 by weight with any balance being impurities. It has been found for such Au/Pd compositions that temperature dependence of its electrical resistance is substantially reduced. In a most preferred embodiment, the Au/Pd ratio is about Au:Pd=1:1.

As previously described, it is preferred that at least region 252 include Au or an Au/Pd alloy. While all of pattern 250 of conductive film 242 may be homogeneously composed of such a material, it should be understood that different parts of film 242 may have an alternative composition. Further, in alternative embodiments, some or all of region 252 may be differently composed. Moreover, at least a portion of film 242 may be comprised of two or more stacked layers of differently composed materials. Substrate 240 includes a material appropriate to prevent electrical short circuiting between spaced apart portions of conductive film 242 carried thereon and that is otherwise selected to be suitable for environmental conditions of subsystem 102. For high temperature applications, substrate 240 may be formed of a ceramic material. In other applications, electrically nonconductive substrate materials common to the electronics industry such as phenolic or polyamide compositions may be utilized. In yet other embodiments, substrate 240 may be multilayered, having an electrically insulating layer between electrically conductive film 242 and other layers of substrate 240; where such other layers may or may not be electrically insulative. In one arrangement, substrate 240 may include a material to enhance thermal conductivity between spaced apart regions of pattern 250 to reduce temperature differences therebetween. Still other arrangements and compositions of substrate 240 are envisioned for other embodiments as would occur to those skilled in the art. Coating 244 may be an erosion resistant silicon nitride, silicon dioxide, thermoplastic or thermoset polymeric resin, or such other material as would occur to those skilled in the art. In still other embodiments, such coatings may not be utilized. In one example, such embodiments may lack a compensation region and otherwise be fabricated to resist wear. In another example, the compensation region may be installed in a manner to prevent substantial erosion by particles, such as placing a compensation film on the opposite side of the substrate relative to the detection region.

In one embodiment, probe 130 is manufactured using photolithographic techniques. For example, conductive film 242 may be initially deposited as a blanket layer on substrate 240. A first photoresist pattern may be deposited on film 242 and photolithographically processed to define pattern 250. The first photoresist is then removed, and a second photoresist pattern applied to prevent covering detection region 252 with coating 244. Indeed, a number of probes 130 may be patterned on a common wafer of substrate material simultaneously and later separated. Nonetheless, in other embodiments, different manufacturing techniques may be utilized to provide probe 130.

Figure 4:
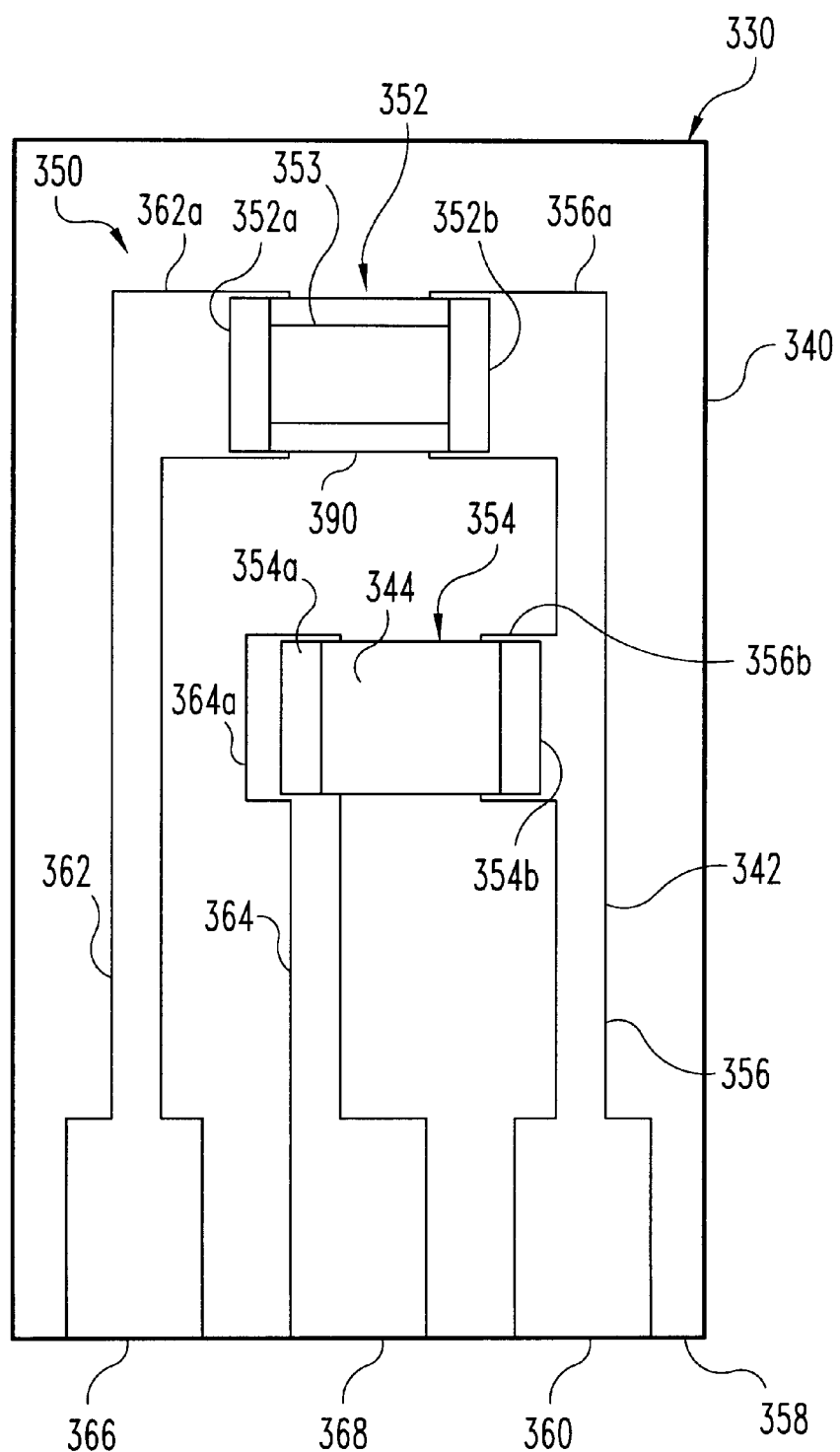
FIG. 4 is an alternative embodiment of a probe according to the present invention.

In FIG. 4, probe 330 is illustrated that is configured to be utilized interchangeably with probe 230 in assembly 104. Probe 330 includes substrate 340 that may be comprised of the same materials as substrate 240. Probe 330 also includes conductive film 342 arranged in pattern 350. Pattern 350 defines traces 356, 362, 364 that terminate at edge 358 in contact areas 360, 366, 368, respectively. Contact areas 360, 366, 368 may be electrically interconnected to monitoring circuit 105 like contact areas 260, 266, 268, respectively. Trace 356 also terminates at component contact regions 356a, 356b. Traces 362, 364 further terminate at component contact regions 362a, 364a, respectively.

Probe 330 includes sensing component 352 and temperature compensating component 354 in place of regions 252, 254, respectively, of probe 230. Together, regions 356a, 362a provide contact pads for electrical interconnection to sensing component 352; and regions 356b, 364a provide contact pads for electrical interconnection to temperature compensating component 354. Components 352, 354 may be connected to respective regions 356a, 362a and 356b, 364b by soldering, a conductive adhesive, or such other technique as would occur to those skilled in the art.

Figure 5:
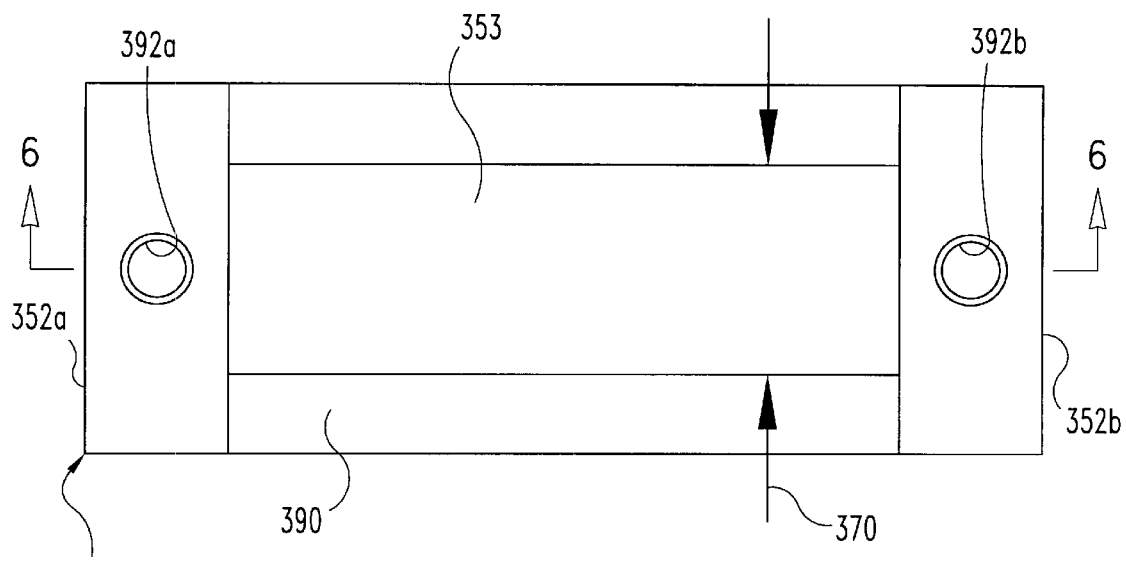
FIGS. 5 and 6 are top and side views, respectively, of a component of the probe shown in FIG. 4; where
Figure 6:
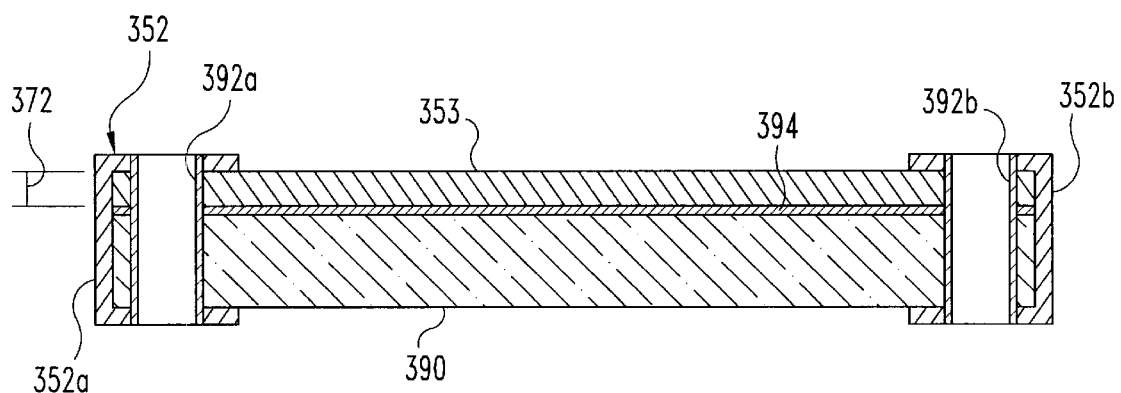

Referring additionally to FIGS. 5 and 6, a top view and corresponding sectional side view of sensing component 352 are further illustrated. Sensing component 352 includes electrically conductive detecting film 353 that is arranged for exposure and gradual erosion by particles from stream 206 in a manner comparable to region 252. Detecting film 353 may be comprised of any of the materials that comprise region 252 of probe 230. Film 353 has minimum width 370 (FIG. 5) and a minimum thickness 372 (FIG. 6). Film 353 is disposed along an electrically insulating component substrate 390. Film 353 is bonded to substrate 390 by bonding layer 394. In one example directed to engine lubricating oil monitoring, film 353 is comprised of an alloy of about 1:1 Au to Pd by weight, and has a minimum width 370 of about 0.030" and a minimum thickness of about 100 nanometers; however, in other examples directed to engine oil and/or other applications, a different composition and/or dimensional arrangement may be utilized. For this example, bonding layer 394 may be in the form of a chrome coating having an electrical resistivity at least 100 times greater than film 353.

Sensing component 352 also includes oppositely disposed, electrically conductive wrap-around end caps 352a, 352b that at least partially enclose corresponding ends of film 353 and substrate 390. End caps 352a, 352b are in electrical contact with film 353 and, in cooperation with substrate 390, define via holes 392a, 392b, respectively. End caps 352a, 352b may be comprised of a material suitable for soldering to regions 356a, 362a, or otherwise arranged for electrical interconnection to traces 356, 362. Via holes 392a, 392b may be utilized to facilitate component placement, testing, and interconnection using techniques known to those skilled in the art.

Temperature compensating component 354 is configured to compensate for changes in the resistance presented by sensing component 352 in response to changes in temperature in a manner comparable to region 254 of probe 230. Compensating component 354 includes an electrically conductive film with substantially the same composition as film 353 of sensing component 352 that is protected from wear by coating 344 (FIG. 4). Compensating component 354 includes conductive, wrap-around end caps 354a, 354b in electrical contact with the film covered by coating 344 arranged to electrically contact regions 356b, 364 of traces 356, 364, respectively.

As in the case of probe 230, probe 330 is arranged to monitor particles entrained in the fluid in correspondence with the erosion of the exposed detecting film 353 of sensing component 352, while the protected film of compensating component 354 accounts for changes in electrical resistance with temperature. Correspondingly, film 342, comprising traces 356, 362, 364, should be arranged to resist wear by particles during exposure of film 353. This arrangement may be accomplished, for example, by material selection, use of a protective coating like coating 344, or both. It should be appreciated that components 352, 354 are arranged to facilitate connection to areas 356a, 362a, and 356b, 364a; respectively, using surface mount soldering techniques. Alternatively, probe 330 may be used without compensating component 354 and/or trace 364.

Thickness of film 353 or film 242 comprising region 252 may vary as would occur to those skilled in the art. In thin film embodiments, it is preferred these films have an initial minimum thickness in a range of about 10 to about 1000 nanometers. More preferably, this initial minimum thickness is in a range of about 20 to about 200 nanometers. Most preferably, for thin film embodiments, the thickness is about 100 nanometers.

Figure 7:
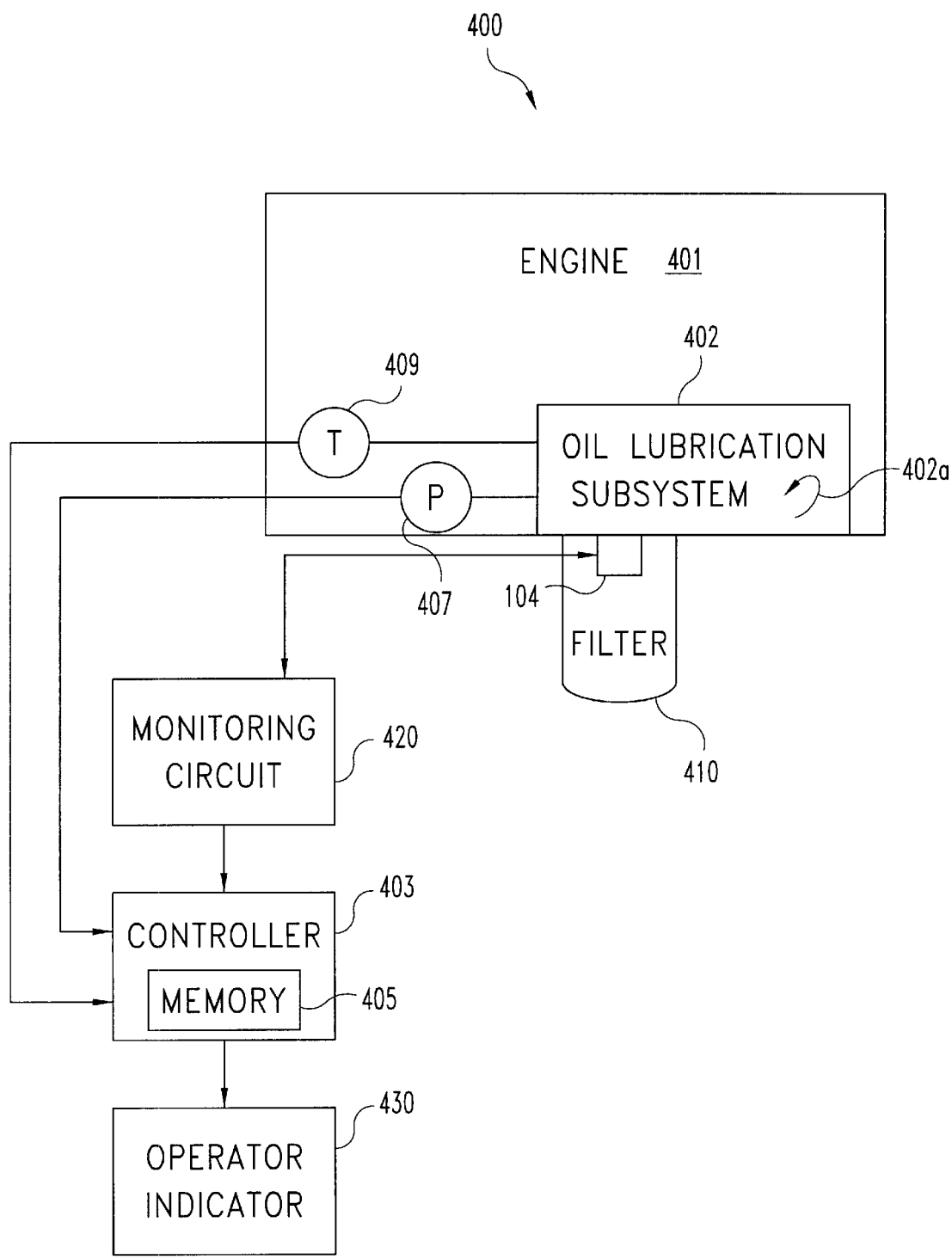
FIG. 7 is a block diagram of an alternative embodiment of an erosion detection system according to the present invention.

Referring to FIG. 7, system 400 of another embodiment of the present invention is shown; where like reference numerals refer to like features with respect to system 100. System 400 includes engine 401 with oil lubrication subsystem 402. Subsystem 402 circulates lubricating oil through engine 401 in the standard manner, as represented by circulation path 402a. Subsystem 402 includes oil filter 410 and probe assembly 104. Probe assembly 104 can be based on probe 230 or probe 330 that is in communication with fluid of subsystem 402 through inclusion in oil filter 410. Filter 410 may be a spin-on type or cartridge type that is changed from time to time, providing a convenient vehicle to replace a worn-out probe 230, 330. Alternatively, filter 410 and/or probe 230, 330 may be arranged for permanent installation. In one embodiment, engine 401 is of the internal combustion variety. For example, the engine can be of a multistroke type driven by reciprocating pistons or rotors. In another example, the engine can be of a gas turbine variety. As an alternative or addition to engine 401, system 400 may include other equipment lubricated by subsystem 402 such as a hydraulic pump, steam turbine, or electric motor, to name just a few.

Figure 8:
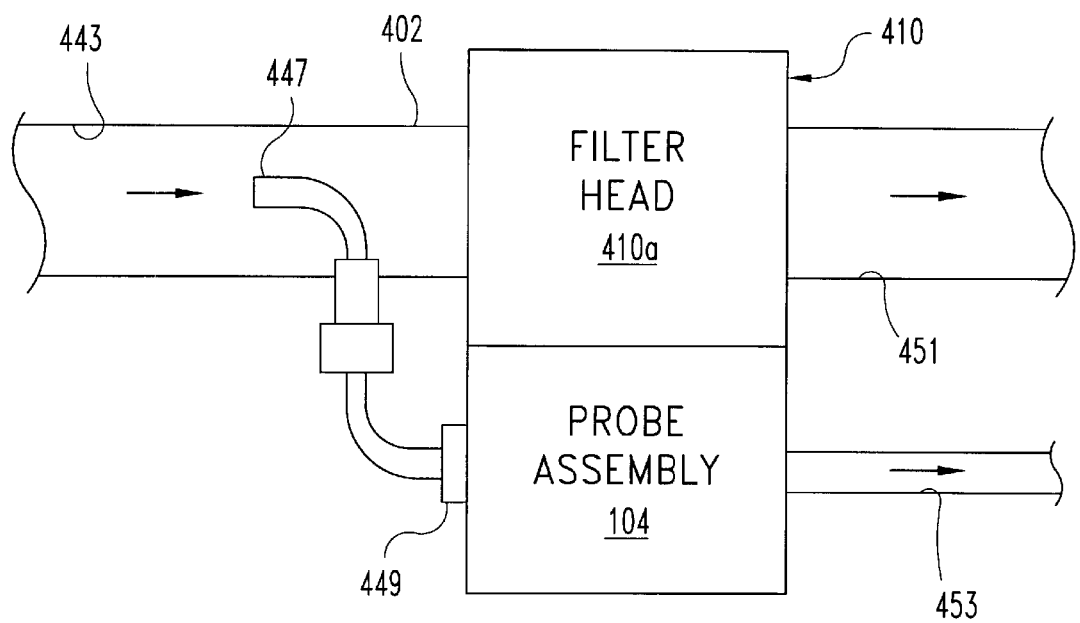
FIG. 8 is a partial schematic view of the probe assembly for the system of FIG. 7.

Referring additionally to FIG. 8, a partial schematic view of probe assembly 104 in relation to filter 410 and subsystem 402 is further shown. In FIG. 8, oil is received from a sump along conduit 443 of subsystem 402 at a predetermined pressure. Sampling port 447 routes a portion of the oil in conduit 443 under pressure to probe assembly 104 via flow limiting device 449. The remaining oil is routed through filter head assembly 410a of filter 410. Oil exiting filter head assembly 410a is routed on to engine 401 through conduit 451 of subsystem 402. Oil exiting probe assembly 104 returns to the sump via conduit 453. In one example, the flow rate in gallons per minute (gpm) is about 30 gpm in conduit 443, and port 447 device 449 are sized to sample oil at about 0.5 gpm with a minimum orifice diameter 221 of about 0.03 to about 0.04 inch.

System 400 also includes monitoring circuit 420, controller 403, and operator indicator 430. Monitoring circuit 420 is electrically coupled to probe assembly 104. Monitoring circuit 420 is also operably connected to controller 403. Controller 403 is, in turn, operably coupled to operator indicator 430. System 400 further includes pressure sensor 407 and temperature sensor 409 to provide respective signals corresponding to Pressure (P) and Temperature (T) of oil in subsystem 402. Signals P and T are input to controller 403.

For system 400, monitoring circuit 420 is arranged to provide one or more signals to controller 403 corresponding to a particle content attribute of oil in subsystem 402. In one embodiment, monitoring circuit 420 provides two voltage signals to controller 403 that each vary with change in $R_S$ and $R_T$, respectively. By way of nonlimiting example, each probe resistance $R_S$, $R_T$ may be connected in series with an external resistor to form a corresponding pair of voltage dividers. When a constant D.C. voltage is applied across both dividers, the voltage incrementally drops across the series of resistances provided by $R_S$ and a first external resistor for one divider, and $R_T$ and a second external resistor for the other divider. For a given divider, if resistance $R_S$ or $R_T$ changes while the voltage and external resistors remain constant, the incremental voltage drops across the individual resistances making up the divider change.

Accordingly, for this example, a pair of voltages corresponding to $R_S$ and $R_T$ may be output as the voltage drops across one of the incremental resistances of the different pair of voltage dividers. These signals may be converted as needed into a format suitable for processing by controller 403 to determine $P_R$. Such processing may include comparing a change in $P_R$ over time (APR) to a threshold limit to determine if an indication to an operator via operator indicator 430 should be changed. For digital processing by controller 403, the voltage signals would typically be converted into a digital form with one or more Analog-to-Digital Converters (A/Ds).

In other embodiments, monitoring circuit 420 may be differently arranged to provide current signals that vary with $R_S$ and $R_C$, or a mixture of current and voltage signals. In still another embodiment, monitoring circuit 420 is arranged to generate an output signal representative of $P_R$ for processing by controller 403. In yet another embodiment not utilizing region 254 or component 354, only a signal corresponding to $R_S$ is provided to controller 403.

Controller 403 may be exclusively dedicated to processing for subsystem 402; however, more typically, controller 403 is configured to perform a number of different routines concerning engine 401 and its operation. As depicted, controller 403 includes memory 405 that may be utilized to store instructions and data. Controller 403 may be comprised of one or more components configured as a single unit. In one example, controller 403 and memory 405 are provided by one or more electronic semiconductor integrated circuit components in the form of a conventional Engine Control Module (ECM) configuration. Alternatively, when of a multi-component form, controller 403 may have one or more components remotely located relative to the others, or otherwise have its components distributed throughout system 400. Controller 403 may be programmable, a state logic machine or other type of dedicated hardware, or a hybrid combination of programmable and dedicated hardware. One or more components of controller 403 may be of the electronic variety defining digital circuitry, analog circuitry, or both. As an addition or alternative to electronic circuitry, controller 403 may include one or more mechanical, hydraulic, pneumatic, or optical elements.

In one embodiment including electronic circuitry, controller 403 has a semiconductor-based, digital integrated processing unit operatively coupled to one or more solid-state memory devices defining, at least in part, memory 405. For this embodiment, memory 405 contains programming to be executed by the processing unit and is arranged for reading and writing of data in accordance with one or more routines executed by controller 403.

Memory 405 may include one or more types of solid-state electronic memory and additionally or alternatively may include the magnetic or optical variety. For example, memory 405 may include solid-state electronic Random Access Memory (RAM), Sequentially Accessible Memory (SAM) (such as the First-In, First-Out (FIFO) variety or the Last-In First-Out (LIFO) variety), Programmable Read Only Memory (PROM), Electrically Programmable Read Only Memory (EPROM), flash memory, or Electrically Eraseable Programmable Read Only Memory (EEPROM); an optical memory (such as a DVD or CD ROM); a magnetically encoded hard disc, floppy disc, tape, or cartridge media; or a combination of any of these types. Also, memory 405 may be volatile, nonvolatile, or a hybrid combination of volatile and nonvolatile varieties.

Besides memory 405, controller 403 may also include any control clocks, interfaces, signal conditioners, filters, limiters, Analog-to-Digital (A/D) converters, Digital-to-Analog (D/A) converters, communication ports, or other types of circuits as would occur to those skilled in the art to implement the present invention.

The response of probe assembly 104 to abrasive particles in oil lubrication system 402 is monitored with monitoring circuit 420 that provides one or more corresponding signals to controller 403 for processing in any of a variety of ways. In one embodiment, controller 403 accounts for variations in oil pressure for lubrication system 402 that can effect the erosion rate of region 252 or film 353 for probes 230, 330, respectively. For such embodiments, controller 403 derives a correction factor from input provided by pressure sensor 407. In another embodiment, controller 403 alternatively or additionally accounts for variations in oil temperature with temperature sensor 409. In yet another embodiment, controller 403 adjusts the input from monitoring circuit 420 according to variations in viscosity of the oil in lubrication system 402 which may be determined with one or more sensors. For example, for typical engine oil, viscosity can be approximated from a predetermined relationship to sensed oil temperature. In still other embodiments, electronic controller 403 adjusts for variations in two or more of temperature, viscosity, and pressure. Such adjustments may be made by reference to a lookup table stored in memory 405, with its values determined empirically or theoretically. Alternatively or additionally, a mathematical expression or other technique could be used to obtain a correction factor for one or more of these conditions. Still, it is recognized that in other embodiments, corrections for such conditions may not be desired.

Whether corrected or not, controller 403 responds to input from monitoring circuit 420 to provide one or more corresponding output signals to operator indicator 430. Operator indicator 430 responds to controller output signals to selectively provide an output to an operator. Operator indicator 430 may be variously configured as described in connection with operator indicator 110.

In an alternative embodiment, the temperature compensation feature of probe 130, 230 may not be desired. Accordingly, fewer connections between monitoring circuits 105, 420 and probe assembly 104 are required. In one example lacking a temperature compensation region or component, detection region 252 or film 353 is comprised of an Au/Pd alloy; however, in other examples, a different composition of region 252 or film 353 can be utilized. In another example lacking compensation, a temperature sensor, such as sensor 409 is utilized to provide temperature compensation. In still other examples, the sensor accuracy and/or the temperature coefficient of resistivity of the corresponding particle detection film may be such that compensation is not desired.

Furthermore, controller 403 may be arranged to provide a number of other operations relative to various sensed parameters of oil lubrication subsystem 402. For example, controller 403 may be configured to store a rate of change history for the particle level detected with probe assembly 104 and extrapolate the amount of usage recommended before the next servicing of engine 401. The amount of usage may be given in terms of time, or in terms of distance for a vehicle application of system 400. This feature may also be utilized to provide notice that detection region 252 of probe 230 or component 352 of probe 330 has become so worn that it needs to be replaced. In a another example, particle levels may be stored and analyzed on an ongoing basis to predict "remaining life" of engine 401. This feature may be used to trigger a major overhaul. Likewise, the particle level information may be stored to verify compliance with warranty conditions for system 400.

When filter 410 is of the type that is replaced from time to time, probe assembly 104 is also typically removed and replaced. For each newly installed probe assembly 104, controller 403 may be arranged to recalibrate particle readings, as required. Indeed, probe assembly 104 and/or filter 410 may be arranged to provide a signal to controller 403 to indicate replacement has occurred.

Figure 9:
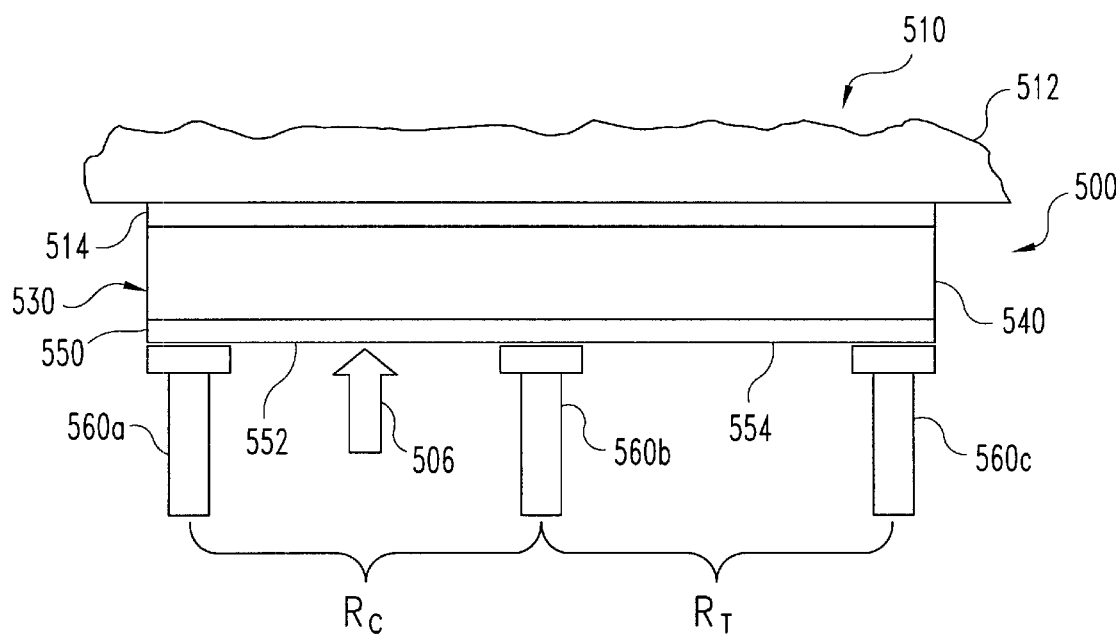
FIG. 9 is a partial schematic view of a particle sensor for a cartridge filter arrangement.

Referring to FIG. 9, a partial schematic view of a probe 530 arrangement for interfacing with an interchangeable cartridge filter 510 for engine 401 is illustrated. Probe 530 is coupled to filter endplate 512 by adhesive layer 514. Probe 530 includes electrically insulating substrate 540 with an electrically conductive film 550 disposed therealong. When exposed to fluid jet 506 entrained with abrasive particles, film 550 gradually erodes. Three spring-loaded electrical contact posts/pins 560a, 560b, 560c contact film 550. Posts 560a, 560b, 560c can be a part of the exchangeable cartridge filter housing. Sensing region 552 is defined between posts 560a, 560b that is exposed to fluid jet 506. Temperature compensation region 554 is defined between posts 560b, 560c. Region 554 is arranged and/or covered to prevent erosion by particles carried in the fluid from which jet 506 is generated. In yet another embodiment, the particle sensor may be provided in the form of a disposable button that is installed in the filter head assembly.

In a further embodiment, multiple particle detection sensors are utilized. For instance, a probe assembly 104 can be incorporated into the air supply subsystem for engine 401 to gather additional information, like differentiating between particles introduced by air subsystem leaks and those resulting from mechanical part failure. This multiple particle sensor approach further augments the data gathering and analyses previously described—especially with regard to a "remaining life" determination.

Figure 10:
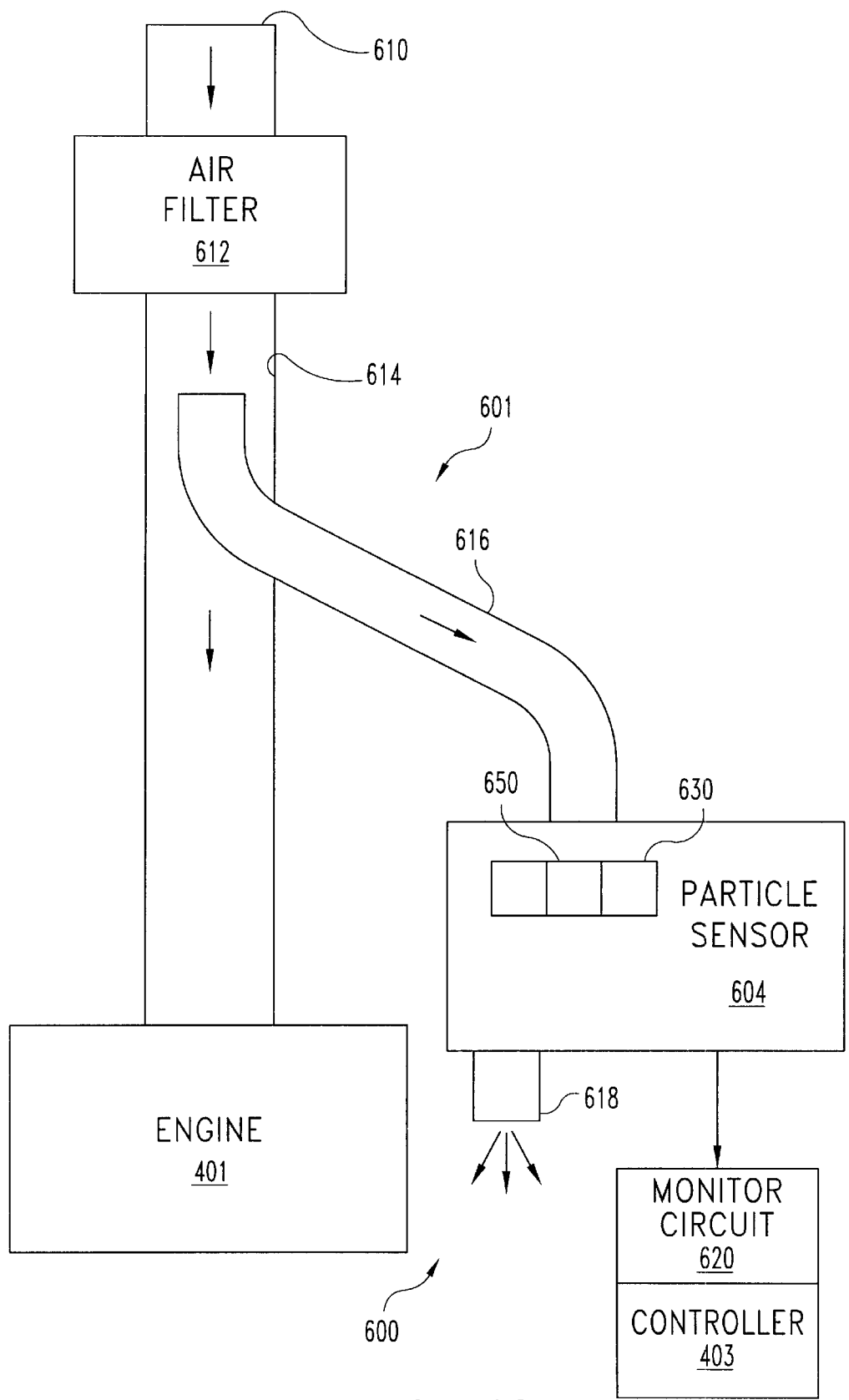
FIG. 10 is a partial, schematic view of an air induction particle detection system.

Referring additionally to FIG. 10, an air induction particle monitoring system 600 is illustrated for engine 401; where like reference numerals represent like features with respect to previously described embodiments. System 600 may be used with or without other particle monitoring devices such as probe assembly 104. System 600 includes air induction system 601 in fluid communication with air particle sensor 604 that may be arranged the same as assembly 104 with orifice diameter 221, gap distance 220, and film width 270 sized to accommodate a gas instead of liquid fluid. Sensor 604 includes probe 630 with sensing film 650 that is arranged to charge its electrical resistance as it is gradually eroded by exposure to particles entrained in air sampled from induction system 601. It has been found that a different sensing film 650 composition may be desired for sensor 604 relative to oil lubrication monitoring applications. In one example, film 650 is comprised of tantalum nitride (TaN). In other examples, different nitride, oxide, or silicide compounds including one or more metal constituents may be utilized, or such other materials as would occur to those skilled in the art.

System 600 includes air intake 610 coupled to air filter 612. Filter 612 provides filtered intake air to conduit 614. Conduit 614 supplies air to engine 401 for mixing with fuel to provide a combustible charge. A compressor, aftercooler, throttle valve, and the like may be positioned along conduit 614 as would occur to those skilled in the art.

Sample port 616 samples air from conduit 614 in a manner suitable to deliver airborne particles to particle sensor 604 that are representative of the type being delivered to engine 401. The sensing film 650 of sensor 604 is accordingly eroded and corresponding resistance changes monitored with monitoring circuit 620. As in the case of probe assembly 104, air from conduit 616 is supplied under pressure and provided from an orifice in the form of a jet that impinges on film 650. Air is discharged from sensor 604 through outlet 618.

Monitoring circuit 620 can be configured the same as monitoring circuit 105, 420 except that it is coupled to sensor 604. Controller 403, previously described, responds to measurements from circuit 620 in accordance with its programming which may include output signals to an operator indicator (not shown) and/or "remaining life" or "next service" predictions, just to name a few arrangements.

All publications, patents, and patent applications cited in this specification are herein incorporated by reference as if each individual publication, patent, or patent application were specifically and individually indicated to be incorporated by reference and set forth in its entirety herein. Further, any theory, mechanism of operation, proof, or finding stated herein is meant to further enhance understanding of the present invention and is not intended to make the scope of the present invention in any way dependent upon such theory, mechanism of operation, proof, or finding. While the invention has been illustrated and described in detail in the drawings and foregoing description, the same is to be considered as illustrative and not restrictive in character, it being understood that only the preferred embodiment has been shown and described and that all changes, equivalents, and modifications that come within the spirit of the inventions defined by following claims are desired to be protected.

What is claimed is:

1. A method, comprising:
    providing a probe including a conductive pathway having a composition including gold;
    directing a jet of a fluid against the conductive pathway, the conductive pathway being eroded by at least a portion of a number of particles carried in the jet; and
    detecting a property of the pathway corresponding to electrical resistance to monitor particle content of the fluid.

2. The method of claim 1, wherein said detecting includes correcting for a variation in viscosity of the fluid.

3. The method of claim 1, wherein said detecting includes correcting for a variation in pressure of the fluid.

4. The method of claim 1, wherein the fluid includes an oil circulating in a lubrication system of an engine and further comprising providing a human detectable indication when particle content of the oil exceeds a threshold determined with said detecting.

5. The method of claim 1, wherein the jet is defined by an orifice having a diameter, the conductive path has a cross-conductive width impinged by the jet, and a ratio of the width to the diameter is between 0.5 and 1.5.

6. The method of claim 1, further comprising:

performing said providing, said directing, and said detecting to determine particle content in a fluid system;

estimating a usage period before servicing the fluid system; and indicating the usage period to an operator.

7. A device, comprising:

a probe to sense particle content in oil of a fluid system, said probe including an electrically insulating substrate and an electrically conductive pathway defined by a metallic film comprising gold, said conductive pathway having at least two electrical contacts arranged for coupling to a monitoring circuit;

wherein said probe includes a mounting structure to removably position said probe in the fluid system, at least a portion of said conductive pathway is exposed to a jet of the oil when said probe is positioned in the fluid system, and said film is composed to be gradually eroded away by particles carried in the oil when exposed to the jet; and whereby a change in the particle content of the oil is determined by monitoring an electrical property of the conductive pathway caused by particle erosion with the monitoring circuit, said property corresponding to electrical resistance of said conductive pathway.

8. The device of claim 7, further comprising an oil filter assembly for removably coupling to the fluid system, said assembly incorporating said probe.

9. A combination, comprising:

a fluid system including a conduit terminating in an orifice to provide a fluid jet;

a probe positioned to be in contact with the fluid jet, said probe including an electrically insulating substrate and a conductive sensing film defining an electrically conductive pathway, said pathway being arranged for exposure to the fluid jet;

an electrical monitoring circuit coupled to said pathway to monitor variation of a property of said pathway corresponding to electrical resistance, said electrical resistance of said pathway changing in accordance with erosion of said pathway by particles carried in the fluid jet; and wherein said orifice has a diameter, said pathway has a cross-conductive width, and a ratio of said width to said diameter is between 0.5 and 1.5.

10. The combination of claim 9, wherein said probe further defines a compensation film on said substrate to compensate for variation of said property with temperature.

11. The combination of claim 9, further comprising an internal combustion engine with said fluid system defining an oil circulation path to lubricate said engine.

12. The combination of claim 11, wherein said probe is contained in an oil filter removably coupled to said fluid system.

13. The combination of claim 11, further comprising an operator indicator coupled to said circuit to provide an indication when particle content of a fluid defining the fluid jet exceeds an acceptable limit.

14. The combination of claim 9, wherein said ratio is between 0.75 and 1.25.

15. A system, comprising:

an engine;

an air induction system to provide air to said engine;

a particle sensor including an electrically conductive particle sensing member in fluid communication with a jet of air from said air induction system; and an electrical monitoring circuit including an electrical pathway, said pathway being at least partially comprised of said particle sensing member, said circuit being operable to monitor variation of a property of said member corresponding to electrical resistance, said electrical resistance of said pathway changing in accordance with erosion of said member by particles provided from said air induction system.

16. The combination of claim 15, wherein said conductive member is in the form of a film comprised of tantalum nitride.

17. The combination of claim 15, further comprising a controller responsive to said circuit to predict remaining life of said engine.

18. The combination of claim 17, further comprising a probe assembly operable to monitor particle content of oil for a lubrication subsystem of said engine, said controller being further responsive to one or more signals from said probe assembly to determine the remaining life of said engine.

* * * * *